(12) United States Patent
Colquhoun

(10) Patent No.: US 10,828,082 B2
(45) Date of Patent: Nov. 10, 2020

(54) ELECTROCAUTERY DEVICE

(71) Applicant: Steven D. Colquhoun, Los Angeles, CA (US)

(72) Inventor: Steven D. Colquhoun, Los Angeles, CA (US)

(*) Notice: Subject to any disclaimer, the term of this patent is extended or adjusted under 35 U.S.C. 154(b) by 121 days.

(21) Appl. No.: 14/616,542

(22) Filed: Feb. 6, 2015

(65) Prior Publication Data

US 2016/0228176 A1 Aug. 11, 2016

(51) Int. Cl.
*A61B 18/00* (2006.01)
*A61B 18/14* (2006.01)
*A61B 18/08* (2006.01)

(52) U.S. Cl.
CPC ........ *A61B 18/082* (2013.01); *A61B 18/1482* (2013.01); *A61B 2018/00595* (2013.01); *A61B 2218/002* (2013.01); *A61B 2218/007* (2013.01)

(58) Field of Classification Search
CPC . A61B 18/00; A61B 18/1402; A61B 18/1482; A61B 2018/0019; A61B 2018/00595; A61B 2018/00916; A61B 2018/1407; A61B 2218/002; A61B 2218/007
See application file for complete search history.

(56) References Cited

U.S. PATENT DOCUMENTS

| | | | | |
|---|---|---|---|---|
| 4,674,498 A * | 6/1987 | Stasz | ................. | A61B 18/1402 604/22 |
| 4,750,902 A * | 6/1988 | Wuchinich | ....... | A61B 17/22012 604/22 |
| 5,254,117 A | 10/1993 | Rigby et al. | | |
| 5,334,183 A | 8/1994 | Wuchinich | | |
| 5,413,575 A * | 5/1995 | Haenggi | ............ | A61B 18/1402 606/39 |
| 5,449,357 A | 9/1995 | Zinnanti | | |
| 5,830,214 A | 11/1998 | Flom et al. | | |
| 6,027,450 A * | 2/2000 | Brown | ........... | A61B 17/320758 600/159 |
| 6,203,537 B1 * | 3/2001 | Adrian | ................... | A61B 18/26 601/4 |
| 6,280,441 B1 | 8/2001 | Ryan | | |
| 6,451,017 B1 | 9/2002 | Moutafis et al. | | |
| 7,160,296 B2 | 1/2007 | Pearson et al. | | |

(Continued)

OTHER PUBLICATIONS

NDT Resource Center, "*Piezoelectric Transducers*", (www.nde-ed.org/EducationResources/CommunityCollege/Ultrasonics/EquipmentTrans/piezotransducers.htm), accessed on Nov. 18, 2014.

(Continued)

*Primary Examiner* — Daniel W Fowler
*Assistant Examiner* — Tigist S Demie
(74) *Attorney, Agent, or Firm* — Lewis Roca Rothgerber Christie LLP

(57) ABSTRACT

An electrocautery device for use in a surgical operation to coagulate tissue and/or organs in a patient. The cautery device includes a sheath defining a longitudinal axis, a handle coupled to a proximal end of the sheath, a cauterizing tip coupled to the distal end of the sheath, and at least one actuator configured to move the cauterizing tip relative to the sheath. The movement of the cauterizing tip is configured to mitigate the risk of tissue or organ adherence to the cauterizing tip during a cauterizing operation.

16 Claims, 2 Drawing Sheets

(56) References Cited

U.S. PATENT DOCUMENTS

| | | |
|---|---|---|
| 7,166,103 B2 | 1/2007 | Carmel et al. |
| 7,717,913 B2 | 5/2010 | Novak et al. |
| 8,133,233 B2 | 3/2012 | Docimo et al. |
| 2002/0147446 A1 | 10/2002 | Ein-Gal |
| 2004/0049216 A1* | 3/2004 | Verdaasdonk ............... A61B 17/320068 606/169 |
| 2005/0107782 A1 | 5/2005 | Reschke |
| 2005/0283150 A1* | 12/2005 | Moutafis .......... A61B 17/32037 606/49 |
| 2006/0079873 A1* | 4/2006 | Scopton ......... A61B 17/320016 606/37 |
| 2009/0287209 A1* | 11/2009 | Matsumoto ........ A61B 18/1492 606/41 |
| 2010/0137751 A1* | 6/2010 | Tadami .............. A61B 18/1402 601/2 |
| 2011/0178547 A1* | 7/2011 | Paul, Jr. ............. A61B 17/0057 606/213 |
| 2011/0230906 A1* | 9/2011 | Modesitt .................. A61B 1/04 606/185 |
| 2013/0211176 A1* | 8/2013 | Habib ................ A61B 18/1492 600/3 |
| 2014/0276813 A1* | 9/2014 | Gambrell ........... A61B 18/1482 606/49 |
| 2015/0327922 A1* | 11/2015 | Dawood ............ A61B 18/1492 606/41 |

OTHER PUBLICATIONS

Woodford, "*Piezoelectricity*", (www.explainthatstuff.com/piezoelectricity.html), Jul. 14, 2014.

International Search Report and Written Opinion for corresponding PCT Application No. PCT/US2016/017014, dated Jun. 24, 2016 (13 sheets).

\* cited by examiner

ELECTROCAUTERY DEVICE

FIELD

The present disclosure relates generally to electrocautery devices and, more particularly, electrocautery devices with one or more of an oscillating or rotating tip, controlled irrigation and suction.

BACKGROUND

Electrocautery devices are commonly used in a variety of surgical operations to control bleeding from tissue and organs. Electrocautery devices typically include a conducting element configured to deliver high-frequency current (e.g., 100 kHz to 4 MHz) to tissues sufficient to generate intracellular heat, tissue desiccation and/or protein denaturation. In this manner, electrocautery devices are configured to cauterize tissues and small vessels, thereby achieving hemostasis. Suction devices are commonly used in conjunction with electrocautery devices to draw blood away from tissues to allow the target bleeding site to be located and cauterized. Suction is also used as an adjunct to cautery inasmuch as flowing blood can overwhelm the effectiveness of cautery.

Used as separate instruments, the use of cautery and suction as described above require two or more hands of operating surgeons. For example, one operating hand may aspirate pooling or flowing blood with a suction device, while a second hand grasps the point of bleeding with conductive forceps and a third hand is required to apply electrocautery energy to the forceps with a conventional electrocautery device. Accordingly, conventional devices require both hands of a surgeon or multiple surgeons or other medical professionals to simultaneously use the electrocautery and suction functions, which can be inefficient and cumbersome. Combined suction/cautery devices are currently available; however, such devices appear to provide these functions in a mutually exclusive manner i.e., the functions are not complementary, and each must be used independent of the other function.

When a conductive suction device is used, cautery energy can be directly applied thereby eliminating one step described above. However, in that circumstance, tissues tend to adhere or "weld" to the suction tip as the point of electrocautery energy delivery. In this specific instance, upon removal of the suction device the hemostatic eschar resulting from cautery is displaced which re-initiates bleeding and is therefore counterproductive. Accordingly, in such a circumstance, to prevent tissue adherence, the surgeon or other medical professional manipulating the metal suction device to which cautery energy is applied, would be required to rapidly and continuously move the instrument against the target site, while a third hand provides saline drip irrigation. Thus, in this circumstance, multiple hands are still required to achieve hemostasis. This latter technique is not well known, is cumbersome, difficult to master and prone to error.

SUMMARY

The present disclosure is directed to various embodiments of an electrocautery device and method for its use. In one exemplary embodiment, this device may provide a conductive suction tip with single handed control of both cautery with motion and drip irrigation at the tip, with the goal of integrating several steps as described above into a single efficient tool. In one embodiment, the electrocautery device includes a sheath defining a longitudinal axis, a handle coupled to a proximal end of the sheath, a cauterizing tip coupled to a distal end of the sheath, and at least one actuator configured to move the cauterizing tip relative to the sheath and a second to provide drip irrigation. In one embodiment, the actuator may include at least one piezoelectric transducer in the cauterizing tip. When an alternating current is applied to the piezoelectric transducer, the cauterizing tip oscillates about an axis perpendicular to the longitudinal axis of the sheath. The piezoelectric transducer may be comprised of any suitable active material, such as a piezoceramic material, a magnetostrictive material, or a piezoelectric crystal. In one embodiment, the alternating current may have a frequency from approximately 100 kHz to approximately 4 MHz. Alternatively the actuator may include a micro-motor in the cauterizing tip. The actuator may include a switch in the handle and a transmission member coupling the switch to the cauterizing tip. In one embodiment, the electrocautery device may also include a suction tube extending from the handle to the tip through the sheath configured to draw fluid away from the tip. In one embodiment, the electrocautery device may also include an irrigation tube extending from the handle to the tip through the sheath configured to deliver fluid to the tip. The electrocautery device may also include a manual actuator on the handle configured to simultaneously or concurrently activate the actuator to move the tip and to deliver high-frequency energy to the cauterizing tip. The electrocautery device may also include a second actuator on the handle configured to deliver the fluid through the irrigation tube. Alternatively, the device may include at least one turbine in the sheath. The turbine may be actuated by fluid or air flowing through the suction tube and/or the irrigation tube. At least a portion of the cauterizing tip may include an electrically conductive material and the sheath may include an electrically insulating material.

This summary is provided to introduce a selection of concepts that are further described below in the detailed description. One or more of the described features may be combined with one or more other described features to provide a workable device.

BRIEF DESCRIPTION OF THE DRAWINGS

These and other features and advantages of embodiments of the present disclosure will become more apparent by reference to the following detailed description when considered in conjunction with the following drawings. In the drawings, like reference numerals are used throughout the figures to reference like features and components. The figures are not necessarily drawn to scale, nor is every feature in the drawings necessarily required to fall within the scope of the described invention.

DETAILED DESCRIPTION

The present disclosure is directed to various embodiments of an electrocautery device. In one embodiment, the electrocautery devices of the present disclosure may include a cauterizing tip configured to deliver high-frequency current during a surgical operation to coagulate tissue and/or organs in a patient and thereby achieve hemostasis. The electrocautery devices of the present disclosure may also include a cauterizing tip configured to be actuated in an oscillatory and/or rotary manner to mitigate the risk of tissue adherence to the cauterizing tip during a cauterizing operation. The electrocautery devices of the present disclosure may also be configured to deliver an irrigation fluid to the tip to further mitigate the risk of tissue adherence to the cauterizing tip during a cauterizing operation and to provide cooling to parenchymal tissues at high cautery settings. The electrocautery devices of the present disclosure may also be configured to draw fluid (e.g., blood or excess irrigation fluid) away from the tip and the cauterization site in the patient simultaneously or concurrently with a cauterizing operation. Accordingly, all or some of suction, cautery, oscillatory/rotary, and irrigation functions of the electrocautery device of the present disclosure may be operated by a single surgeon with one hand.

Figure 1:
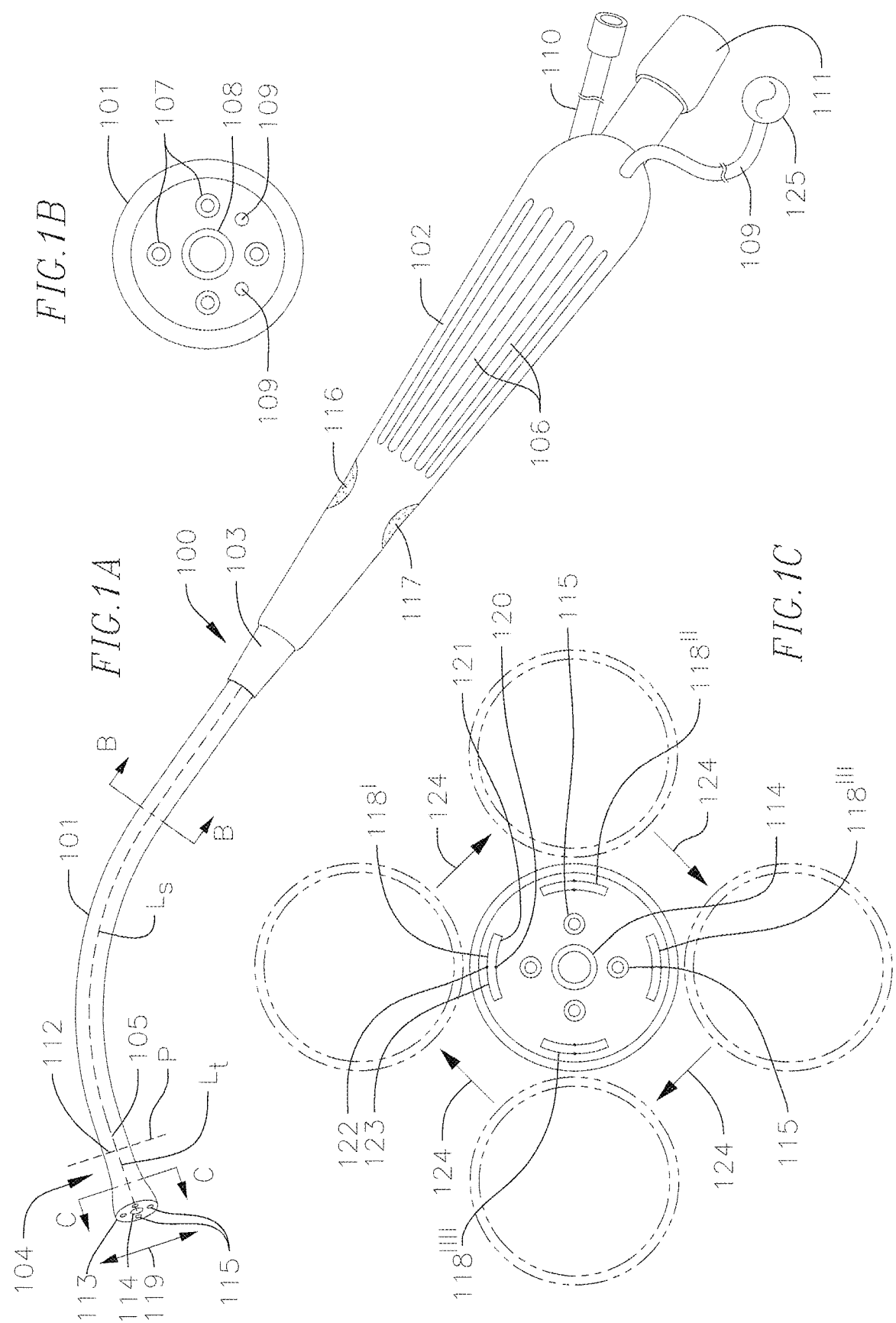
FIG. 1A is a side view of an electrocautery device according to one embodiment of the present disclosure including a cauterizing tip, a sheath, and a handle.
FIG. 1B is a cross-sectional view of the electrocautery device illustrated in FIG. 1A taken along line B-B.
FIG. 1C is a cross-sectional view of the electrocautery device illustrated in FIG. 1A taken along line C-C showing a plurality of piezoelectric transducers configured to move the cauterizing tip.

With reference now to FIGS. 1A and 1B, an electrocautery device 100 according to one embodiment of the present disclosure includes an elongated sheath 101, a handle portion 102 coupled to a proximal end 103 of the sheath 101, and a cauterizing tip 104 coupled to a distal end 105 of the sheath 101. The handle portion 102 and the sheath 101 may be integrally formed (e.g., by injection molding) or separately formed and coupled together by any suitable process, such as, for instance, friction stir welding. In the illustrated embodiment, the sheath 101 is a thin-walled, hollow member that functions as a conduit for delivering a plurality of lines and/or tubes from the handle to the cauterizing tip 104, as described in more detail below. The sheath 101 also defines a longitudinal axis $L_s$. Additionally, in the illustrated embodiment, the handle portion 102 is tapered and may include a plurality of ridges or grooves 106 to facilitate ergonomic handling and prevent mishandling, respectively, of the electrocautery device 100 by a surgeon or other medical professional.

With reference to the embodiment illustrated in FIG. 1B, the sheath 101 houses a plurality of irrigation tubes 107 configured to deliver irrigation fluid (e.g., saline) to the cauterizing tip 104, a suction tube 108 configured to draw fluid (e.g., blood or excess irrigation fluid) away from the cauterizing tip 104, and at least one electrical line 109 (e.g., a cable) configured to deliver electrical current (e.g., high-frequency current from approximately 100 kHz to approximately 4 MHz) to the cauterizing tip 104. Delivery of the irrigation fluid to the cauterizing tip 104 is configured to mitigate the risk of tissue adherence to the cauterizing tip 104 during a cauterizing operation. The suction tube 108 is configured to draw fluid away from the cauterizing tip 104 and the target site in the patient to allow the surgeon or other medical professional to locate the source of the bleeding to be cauterized. Although in the illustrated embodiment the electrocautery device 100 includes a single suction tube 108 and four irrigation tubes 107, in one or more embodiments, the electrocautery device 100 may include any other suitable number of suction tubes 108 and any other suitable number of irrigation tubes 107. Additionally, in one or more embodiments, the electrocautery device 100 may be provided without the irrigation tubes 107. Furthermore, although in the illustrated embodiment the electrocautery device 100 includes irrigation and suction tubes 107, 108 that are separate from the sheath 101 and the handle 102, in one or more embodiments, the irrigation tubes 107 and/or the suction tube 108 may be integrally defined in the sheath 101 and the handle 102. For example, the sheath 101 and the handle 102 of the electrocautery device 100 may define a plurality of lumens (e.g., smooth bores) through which irrigation fluid is pumped to the cauterizing tip 104 and/or through which fluid is drawn away from the cauterizing tip 104.

With reference now to the embodiment illustrated in FIG. 1A, proximal ends of the irrigation tubes 107 are coupled to an irrigation port 110 configured to facilitate quick-release connection to and disconnection from an irrigation supply source (e.g., a saline source). A proximal end of the suction tube 108 is coupled to a connector 111 (e.g. a port) configured to facilitate quick-release connection to and disconnection from a suction device (e.g., a pump or a vacuum). Additionally, a proximal end of the electrical line 109 is coupled to an electrical connector configured to facilitate quick-release connection to and disconnection from a standard electrosurgical power supply 125. Accordingly, in the illustrated embodiment, the electrocautery device 100 may be disconnected from the irrigation supply source, the suction device, and the power supply 125 following a surgical operation and disposed of, and a new electrocautery device 100 may then be reconnected to the irrigation supply source, the suction device, and the power supply 125 prior to a subsequent surgical operation. That is, to ensure the electrocautery device 100 is sterile during a surgical operation, the cautery devices 100 of the present application may be disposable such that a new electrocautery device 100 is used for each surgical operation. In one or more alternate embodiments, the electrocautery device 100 may be reused and disinfected in any suitable manner, such as by ultraviolet irradiation, between surgical operations.

With continued reference to an exemplary embodiment illustrated in FIG. 1A, the cauterizing tip 104 is generally frusto-conical and includes a narrower proximal end 112 that tapers to a wider distal end 113. The cauterizing tip 104 also defines a longitudinal axis $L_t$. In the illustrated embodiment, the longitudinal axis $L_t$ of the cauterizing tip 104 is coaxial with the longitudinal axis $L_s$ of the sheath 101. Additionally, in the illustrated embodiment, the wider distal end 113 of the cauterizing tip 104 is smooth (e.g., rounded). In one or more alternate embodiments, the cauterizing tip 104 may have any other shape suitable for the nature of the surgical operations with which cauterizing device 100 is intended to be used. In the illustrated embodiment, the wider distal end 113 of the cauterizing tip 104 also defines a suction port 114 and a plurality of irrigation ports 115 arranged around the suction port 114. The suction port 114 and the plurality of irrigation ports 115 are aligned with the suction tube 108 and the irrigation tubes 107, respectively. In one embodiment, the suction port 114 and the irrigation ports 115 may receive distal ends of the suction tube 108 and the irrigation tubes 107, respectively. Additionally, in the illustrated embodiment, the suction port 114 is coaxial or substantially coaxial with the sheath 101 (i.e., the suction port 114 is aligned with the longitudinal axis $L_s$ of the sheath 101) and the irrigation ports 115 are arranged off of the longitudinal axis $L_s$ of the sheath 101. Additionally, in one or more embodiments, the suction and irrigation ports 114, 115 may be arranged in any other suitable configuration on the cauterizing tip 104. Although in the illustrated embodiment the cauterizing tip 104 defines one suction port 114 and four irrigation ports 115, in one or more embodiments, the cauterizing tip 104 may define any other number of suction ports 114 and irrigation portions 115 corresponding to the number of suction tubes 108 and irrigation tubes 107. For instance, in one embodiment in which the electrocautery device 100 does not include irrigation tubes 107, the cauterizing tip 104 may be provided without the irrigation ports 115.

With continued reference to the exemplary embodiment illustrated in FIG. 1A, the handle 102 includes an upper actuator 116 (e.g., a button) configured to allow selective delivery of electrical current to the cauterizing tip 104 and a lower actuator 117 (e.g., a button) configured to allow selective delivery of irrigation fluid to the cauterizing tip 104. As described in more detail below, when the upper actuator 116 is actuated (e.g., depressed), electrical current flows from the power supply to the cauterizing tip 104 and thereby simultaneously or concurrently moves (e.g., oscillates and/or rotates) the cauterizing tip 104 and delivers high-frequency current (e.g., 100 kHz to 4 MHz) to the cauterizing tip 104 to cauterize tissue and/or organs and thereby achieve hemostasis. In one embodiment, the upper actuator 116 is coupled to a mechanical switch (e.g., a push-button switch) such that actuation of the upper actuator 116 closes a circuit and thereby permits electrical current to flow from the power supply to the cauterizing tip 104. When the lower actuator 117 is actuated (e.g., depressed), irrigation fluid flows from the irrigation fluid source, through the irrigation tubes housed in the handle 102 and the sheath 101, and out through the plurality of irrigation ports 115 in the cauterizing tip 104 to the cauterization site in the patient. In one embodiment, the lower actuator 117 may be coupled to electrically actuatable valve such that actuation of the lower actuator 117 opens the valve and thereby permits the irrigation fluid to flow through the electrocautery device 100.

With reference now to the exemplary embodiment illustrated in FIG. 1C, the cauterizing tip 104 includes one or more piezoelectric transducers 118 configured to move (e.g., oscillate) the cauterizing tip 104 when electrical current is supplied to the piezoelectric transducers 118. As described in more detail below, the characteristics of the movement of the cauterizing tip 104 depends on the number and arrangement of the piezoelectric transducers 118 in the cauterizing tip 104, the type of current (e.g., direct current or alternating current) supplied to the piezoelectric transducers 118, and other characteristics of the current supplied to the piezoelectric transducers 118 (e.g., the input frequency of the current). Each of the piezoelectric transducer 118 includes polarized molecules (i.e., positively charged molecules and negatively charged molecules). The piezoelectric transducers 118 may be made out of any suitable polarized material, such as, for instance, a piezoceramic material (e.g., lead zirconate titanate or barium titanate), a magnetostrictive material, or a piezoelectric crystal (e.g. quartz). Accordingly, when electric current is applied across the oppositely charged portions of the piezoelectric transducers 118, the piezoelectric transducers 118 mechanically deform as the polarized molecules align themselves with the supplied electric field (i.e., the supplied electric field creates induced dipoles within the piezoelectric transducers 118 that create mechanical strain on the piezoelectric transducers 118). The displacement of the positive molecules in the direction of the electric field and the displacement of the negative molecules in the opposite direction results in the elongation of the piezoelectric transducers 118 in the direction of the applied electric field and corresponding narrowing in a direction orthogonal to the applied electric field. This electrostriction of the one or more piezoelectric transducers 118 causes the cauterizing tip 104 to move (e.g., oscillate).

In one embodiment, the one or more piezoelectric transducers 118 are arranged on the cauterizing tip 104 such that supplying electric current to the piezoelectric transducers 118 causes the distal end 113 of the cauterizing tip 104 to move/pivot (arrow 119) about an axis P perpendicular to the longitudinal axes $L_s$, $L_t$ of the sheath 101 and the cauterizing tip 104. For instance, in one embodiment, the distal end 113 of the cauterizing tip 104 may be configured to pivot (arrow 119) in a plane extending through the upper and lower actuators 116, 117, although in one or more embodiments, the distal end 113 of the cauterizing tip 104 may be configured to pivot in any other suitable plane.

Additionally, in one exemplary embodiment, alternating current (AC) may be supplied from the power supply 125 to the piezoelectric transducers 118 such that the distal end 113 of the cauterizing tip 104 pivots (arrow 119) in an oscillatory manner (e.g., the distal end 113 of the cauterizing tip 104 repeatedly pivots up and down). When AC is supplied to the one or more piezoelectric transducers 118, the piezoelectric transducers 118 vibrate in an oscillatory manner at the same frequency as the input current. Additionally, the cauterizing tip 104 may be configured to oscillate (arrow 119) at any suitable rate depending, for instance, on the composition of the tissue or organs the electrocautery device 100 is intended to cauterize. For instance, the human liver is particularly prone to adhering to a cauterizing element and to tearing when the cauterizing element is detached from the adhered portion of the liver and therefore the cauterizing tip 104 may be configured to rapidly oscillate when the cauterizing device 100 is intended to be used to cauterize the liver. For instance, in one or more embodiments, the frequency of the input current may be within the radio frequency (RF) range (i.e., from approximately 3 kHz to approximately 300 GHz) such that the cauterizing tip 104 is configured to oscillate (arrow 119) at a frequency from approximately 3 kHz to approximately 300 GHz. In one embodiment, the frequency of the input current may be within the microwave spectrum (i.e., from approximately 0.3 GHz to approximately 300 GHz) such that the cauterizing tip 104 is configured to oscillate (arrow 119) at a frequency from approximately 0.3 GHz to approximately 300 GHz. In another embodiment, the frequency of the input current may be from approximately 100 kHz to approximately 4 MHz.

Additionally, the one or more piezoelectric transducers 118 may be either actuated simultaneously, concurrently or sequentially. In one embodiment, the piezoelectric transducers 118 may be sequentially actuated such that the cauterizing tip 104 is deflected along a desired path. For instance, in the embodiment illustrated in FIG. 1C, the cauterizing tip 104 includes an upper piezoelectric transducer 118', a right piezoelectric transducer 118'', a lower piezoelectric transducer 118''', and a left piezoelectric transducer 118'''' arranged in a circular pattern (i.e., four piezoelectric transducers 118'-118'''' arranged in a circumferential or circular array). Additionally, in the illustrated embodiment, each of the electrical lines 109 includes an inner electrode 120 connected to an inner surface 121 of one of the piezoelectric transducers 118'-118'''' and an outer electrode 122 connected to an outer surface 123 of the piezoelectric transducer

118'-118''''. Accordingly, when the upper actuator 116 is actuated (e.g., the upper button is depressed) current is applied across the inner and outer surfaces 121, 123 of the piezoelectric transducers 118'-118''''. Thus, when current is supplied sequentially to the upper, right, lower, and left transducers 118'-118'''', respectively, the distal end 113 of the cauterizing tip 104 will deflect or move (arrow 124) in a circular manner, as illustrated by the dashed lines in FIG. 1C. If the current is rapidly sequenced between the upper, right, lower, and left piezoelectric transducers 118'-118'''', the distal end 113 of the cauterizing tip 104 may rotate smoothly in a circular manner. In one or more embodiments, the piezoelectric transducers 118 may be arranged in any other suitable orientation in the cauterizing tip 104 and the electrodes 120, 122 may be positioned on the piezoelectric transducers 118'-118'''' in any other suitable arrangement depending on the desired movement of the distal end 113 of the cauterizing tip 104 when current is supplied to the piezoelectric transducers 118'-118''''.

Additionally, in one embodiment, the cauterizing tip 104 may be made out of any suitable electrically conductive material such that the high-frequency current (e.g., 100 kHz to 4 MHz) supplied by the electrosurgical power supply 125 is delivered through the cauterizing tip 104 and to the target site in the patient. In one embodiment, the cauterizing tip 104 may be made out of metal (e.g., stainless steel), although in one or more embodiments, the cauterizing tip 104 may be made out of any other suitable bio-compatible material having a sufficiently high electrical conductivity. In one embodiment, the current supplied to move (e.g., oscillate and/or rotate) the cauterizing tip 104 is delivered to the target site in the patient through the cauterizing tip 104 (e.g., depressing the upper actuator 116 actuates the motion of the cauterizing tip 104 and also delivers high-frequency current through the cauterizing tip 104 to cauterize the target site in the patient). Accordingly, in one embodiment, the movement (e.g., oscillation and/or rotation) of the cauterizing tip 104 and the delivery of high-frequency cauterizing current to the cauterizing tip 104 occur simultaneously or concurrently. In one or more alternate embodiments, the movement of the cauterizing tip 104 and the delivery of high-frequency cauterizing current to the cauterizing tip 104 may be actuated independently (e.g., the electrocautery device 100 may include a separate actuator and separate electrical lines coupled to the cauterizing tip 104 to deliver high-frequency cauterizing current to the cauterizing tip 104). Additionally, in one embodiment, the electrocautery device 100 may include a voltage/current level adjustment device permitting an operator to adjust the voltage/current supplied to the cauterizing tip 104, and thereby changing the cauterizing energy supplied to the target site in the patient and/or adjusting the movement of the cauterizing tip 104 (e.g., changing the frequency at which the cauterizing tip 104 moves). Additionally, in one embodiment, the sheath 101 and/or the handle 102 are made of an electrically insulating material, such as, for instance, plastic, to prevent the sheath 101 and/or the handle 102 from conducting the high-frequency frequency current delivered to the cauterizing tip 104 from the electrosurgical power supply 125. Additionally, in one embodiment, the sheath 101 is made out of a flexible material such that the sheath 101 is configured to bend or flex when the cauterizing tip 104 is actuated to move (e.g., oscillate and/or rotate). For instance, the sheath 101 may be configured to flex about an axis perpendicular to the longitudinal axes $L_s$, $L_t$ of the sheath 101 and the cauterizing tip 104.

Figure 2:
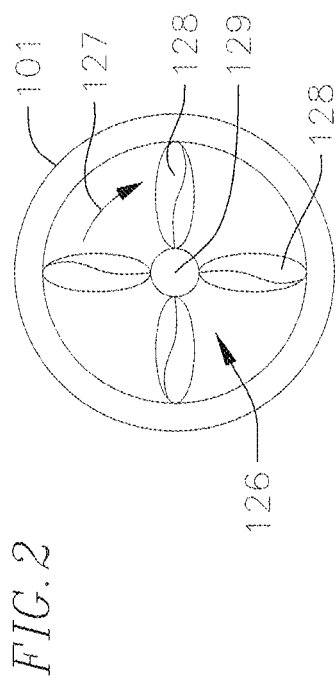
FIG. 2 is a cross-sectional view of the electrocautery device illustrated in FIG. 1A taken along line C-C showing a turbine configured move the cauterizing tip according to one embodiment of the present disclosure.

In one or more embodiments, the electrocautery device 100 may have any other suitable type of actuator for actuating the cauterizing tip 104 in an oscillatory or rotary manner. In the embodiment illustrated in FIG. 2, the electrocautery device 100 includes at least one in-line turbine 126 (e.g., an impeller) housed in the sheath 101. In one embodiment, the turbine 126 may be at least partially within the suction tube 108 such that fluid flowing through the suction tube 108 rotates (arrow 127) the turbine 126 (e.g., blood and/or excess irrigation fluid drawn through the suction tube 108 actuates the turbine 126). In one or more embodiments, the turbine 126 may be at least partially within one or more of the irrigation tubes 107 such that irrigation fluid flowing through the one or more irrigation tubes 107 rotates (arrow 127) the turbine 126. In one or more embodiments, the turbine 126 may be actuated (arrow 127) by any other suitable mechanism, such as, for instance, by an electric motor electrically coupled to the turbine 126. In the illustrated embodiment, the turbine 126 is configured to rotate (arrow 127) about the longitudinal axis $L_s$ of the sheath 101.

In the illustrated embodiment, the turbine 126 includes a plurality of blades 128 radially arranged around a hub 129. In one embodiment, the turbine 126 may be unbalanced or eccentric such that the rotation (arrow 127) of the turbine 126 imparts movement (e.g., vibration) to the cauterizing tip 104. The vibration from the rotating turbine 126 may be transmitted to the cauterizing tip 104 through the sheath 101 and/or the suction tube 108. In one embodiment, one or more of the blades 128 may be more heavily weighted than the other blades 128 such that the turbine 126 is unbalanced and will impart movement (e.g., vibration) to the cauterizing tip 104 when the turbine 126 is rotated (arrow 127). In one or more embodiments, the blades 128 may be non-uniformly spaced around the hub 129 such that the turbine 126 is unbalanced and will impart movement (e.g., vibration) to the cauterizing tip 104 when the turbine 126 is rotated (arrow 127). Accordingly, the cauterizing tip 104 will tend to deflect in the direction of the one or more heavily weighted blades 128 and/or the more closely spaced blades 128 as the turbine 126 is rotated (arrow 127). In one or more embodiments, the turbine 126 may have any other suitable type or kind of asymmetry or eccentricity configured to impart movement to the cauterizing tip 104 when the turbine 126 is rotated (arrow 127), such as, for instance, difference shapes and/or sizes of the blades 128.

Figure 3:
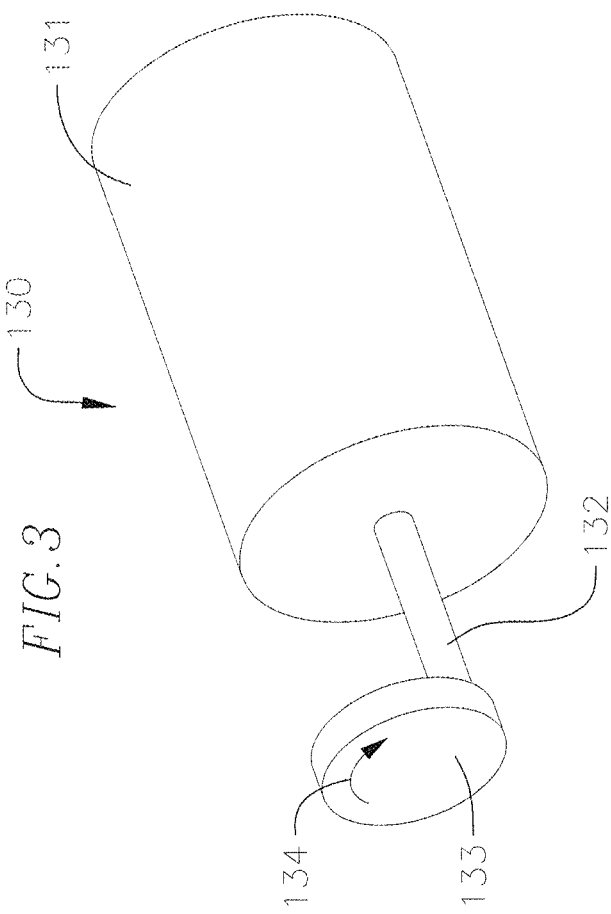
FIG. 3 is a perspective view of an exemplary micro-motor configured to move the cauterizing tip according to one embodiment of the present disclosure.

In another embodiment illustrated in FIG. 3, the electrocautery device 100 includes at least one micro-motor 130 in the cauterizing tip 104. In another embodiment, the micro-motor 130 may be located at any other suitable location within the electrocautery device 100, such as, for instance, within the sheath 101 proximate the cauterizing tip 104 or in the handle 102. In the illustrated embodiment, the micro-motor 130 includes a motor 131, an output shaft 132 configured to be driven by the motor 131, and an eccentric cam or lobe 133 coupled to the output shaft 132. When the output shaft 132 is driven by the motor 131, the cam 133 is rotated (arrow 134) about a longitudinal axis of the output shaft 132. The eccentricity of the cam 133 is configured to impart movement (e.g., vibration) to the cauterizing tip 104 when the cam 133 is rotated (arrow 134) by the motor 131. The micro-motor 130 may be electrically coupled to the upper actuator 116 such that the actuation (e.g., depression) of the upper actuator 116 simultaneously delivers high-frequency current to the target site in the patient to achieve hemostasis and actuates the micro-motor 130 to move the cauterizing tip 104 to mitigate the risk of tissue or organ adherence to the cauterizing tip 104 during the cauterizing operation.

Figure 4:
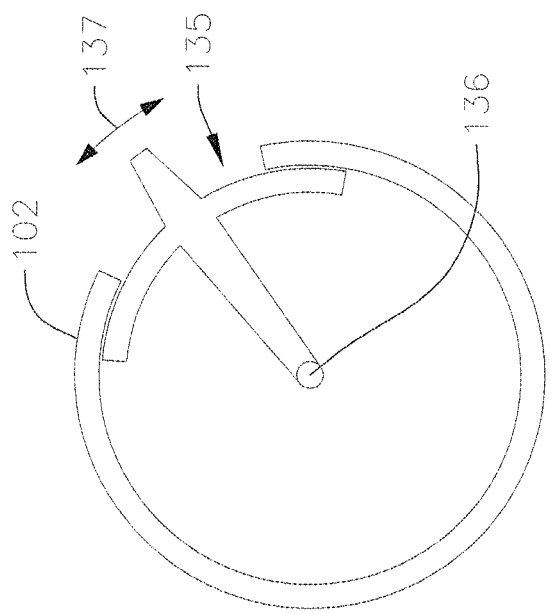
FIG. 4 is a cross-sectional view of an exemplary actuator in the handle configured to move the cauterizing tip according to one embodiment of the present disclosure.

In a further embodiment illustrated in FIG. 4, the electrocautery device 100 includes a mechanical actuator 135 coupled to the handle 102. In one embodiment, the actuator 135 may be a wheel or switch rotatably coupled to the handle 102. In one embodiment, the actuator 135 may include a ratcheting mechanism. In the illustrated embodiment, the actuator 135 is coupled to the cauterizing tip 104 by a transmission member 136 housed in the sheath 101 and the handle 102 (e.g., the transmission member may be a flexible sleeve extending through the handle 102 and the sheath 101). The transmission member 136 is configured to deliver or transmit the movement of the mechanical actuator 135 to the cauterizing tip 104. Accordingly, in one embodiment, a surgeon or other medical professional may move the cauterizing tip 104 by moving (arrow 137) the mechanical actuator 135 back and forth in a reciprocal manner (e.g., rotating the wheel back and forth in opposite directions or flipping the switch back and forth). In one embodiment, the mechanical actuator 135 may be positioned on the handle 102 such that the surgeon can ergonomically and simultaneously or concurrently operate the upper actuator 116 to deliver high-frequency current to cauterize the target site in the patient and operate the mechanical actuator 135 to move the cauterizing tip 104 to mitigate the risk of tissue or organ adherence to the cauterizing tip 104 during the cauterizing operation. For instance, in one embodiment, the upper actuator 116 and the mechanical actuator 135 may be positioned on the handle 102 such that the upper actuator 116 may be depressed by the surgeon's thumb and the mechanical actuator 135 may be actuated by the surgeon's index finger. In another embodiment, the upper actuator 116 may be integrated into the mechanical actuator 135.

The described electrocautery devices may beneficially be used for cauterizing a target area of tissue or organ. In one embodiment, the user grasps the handle of the electrocautery device with one hand, applies the cauterizing tip to the target area to be cauterized and concurrently activates the cauterizing tip and the suction device for cauterizing and suctioning fluid from the target area. The user may further concurrently actuate the cauterizing tip to oscillate or move the tip relative to the sheath, thereby reducing or minimizing adherence of the tip to the target tissue or organ, and enabling the user to remove the cauterizing tip from the target area. In another embodiment, the user may use the devices to irrigate the target area with fluid. The various cycles of cauterization, suction, oscillation and irrigation may be performed manually by the user or part of an automated or timed sequence in which two or more of the functions are concurrently actuated via one or more actuating buttons on the device.

While this invention has been described in detail with particular references to embodiments thereof, the embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention. Although relative terms such as "outer," "inner," "upper," "lower," and similar terms have been used herein to describe a spatial relationship of one element to another, it is understood that these terms are intended to encompass different orientations of the various elements and components of the invention in addition to the orientation depicted in the figures. Additionally, as used herein, the term "substantially," "generally," and similar terms are used as terms of approximation and not as terms of degree, and are intended to account for the inherent deviations in measured or calculated values that would be recognized by those of ordinary skill in the art. Furthermore, as used herein, when a component is referred to as being "on" or "coupled to" another component, it can be directly on or attached to the other component or intervening components may be present therebetween. Further, any described feature is optional and may be used in combination with one or more other features to achieve one or more benefits.

What is claimed is:

1. A cautery device for mitigating adherence of the cautery device upon cauterization of a target area, the target area being a tissue or an organ with flowing blood thereon, the cautery device comprising:
   a sheath having a distal end and a proximal end opposite the distal end, the sheath defining a longitudinal axis;
   a handle coupled to the proximal end of the sheath;
   a cauterizing tip coupled to the distal end of the sheath for applying a current to the target area, the cauterizing tip having a circular shape;
   a suction tube extending through the sheath to the cauterizing tip with a suction opening in a central position of the circular shape of the cauterizing tip, the suction tube configured to draw fluid away from the cauterizing tip; and
   at least one actuator configured to oscillate the cauterizing tip about an axis perpendicular to the longitudinal axis of the sheath concurrently with application of the current to cauterize the target area and mitigate tissue adherence of the target area to the cauterizing tip,
   wherein the at least one actuator comprises at least one piezoelectric transducer in the cauterizing tip, and wherein the piezoelectric transducer oscillates the cauterizing tip to mitigate tissue adherence of the target area to the tip;
   wherein the at least one piezoelectric transducer comprises a plurality of piezoelectric transducers arranged in a circular array, and wherein, when electric current is sequentially applied to the plurality of piezoelectric transducers, a distal end of the cauterizing tip oscillates about the longitudinal axis.

2. The cautery device of claim 1, wherein the at least one piezoelectric transducer comprises an active material selected from the group of materials consisting of a piezoceramic material, a magnetostrictive material, and a piezoelectric crystal.

3. The cautery device of claim 1, wherein the alternating current has a frequency from approximately 100 kHz to approximately 4 MHz.

4. The cautery device of claim 1, further comprising an irrigation tube extending from the handle to the cauterizing tip through the sheath, the irrigation tube configured to deliver fluid to the cauterizing tip.

5. The cautery device of claim 4, wherein the at least one actuator comprises a first actuator on the handle configured to concurrently actuate the actuator to move the cauterizing tip and to deliver high-frequency energy to the cauterizing tip.

6. The cautery device of claim 5, wherein the at least one actuator further comprises a second actuator on the handle configured to deliver the fluid through the irrigation tube.

7. The cautery device of claim 1, wherein at least a portion of the cauterizing tip comprises an electrically conductive material.

8. The cautery device of claim 1, wherein the sheath comprises an electrically insulating material.

9. A method of using the cautery device of claim 1 for mitigating adherence of the cautery device upon cauterization of a target area, the target area being a tissue or an organ with flowing blood thereon, the method comprising:
applying the cauterizing tip to the target area;
concurrently activating the cauterizing tip and the suction tube for cauterizing and suctioning fluid from the target area; and
concurrently actuating the cauterizing tip to oscillate the cauterizing tip about the axis perpendicular to the longitudinal axis of the sheath, applying the current to the target area, and moving the cauterizing tip away from the target area.

10. The method of claim 9 wherein the cautery device further comprises an irrigation tube having an end directed in the vicinity of the cauterizing tip, the method further comprising directing fluid toward the target area.

11. The method of claim 9, further comprising oscillating the cauterizing tip while removing the cauterizing tip from the target area.

12. The method of claim 9, wherein the target area is the liver.

13. The cautery device of claim 1, wherein the distal end is wider than the proximal end.

14. A cautery device for mitigating adherence of the cautery device upon cauterization of a target area, the target area being a tissue or an organ with flowing blood thereon, the cautery device comprising:
a sheath having a distal end and a proximal end opposite the distal end, the sheath defining a longitudinal axis;
a handle coupled to the proximal end of the sheath;
a cauterizing tip coupled to the distal end of the sheath for applying a current to the target area, the cauterizing tip having a circular shape;
a suction tube extending through the sheath to the cauterizing tip with a suction opening in a central position of the circular shape of the cauterizing tip, the suction tube configured to draw fluid away from the cauterizing tip; and
at least one actuator configured to oscillate the cauterizing tip about an axis perpendicular to the longitudinal axis of the sheath concurrently with application of the current to cauterize the target area and mitigate tissue adherence of the target area to the cauterizing tip, the at least one actuator comprising
a switch in the handle; and
a transmission member coupling the switch to the cauterizing tip,
wherein the transmission member is configured to transmit movement of the switch to the cauterizing tip;
wherein the at least one actuator comprises at least one piezoelectric transducer in the cauterizing tip, and wherein the piezoelectric transducer oscillates the cauterizing tip to mitigate tissue adherence of the target area to the tip;
wherein the at least one piezoelectric transducer comprises a plurality of piezoelectric transducers arranged in a circular array, and wherein, when electric current is sequentially applied to the plurality of piezoelectric transducers, a distal end of the cauterizing tip oscillates about the longitudinal axis.

15. A cautery device for mitigating adherence of the cautery device upon cauterization of a target area, the target area being a tissue or an organ with flowing blood thereon, the cautery device comprising:
a sheath having a distal end and a proximal end opposite the distal end, the sheath defining a longitudinal axis;
a cauterizing tip coupled to the distal end of the sheath for applying a current to the target area, the cauterizing tip having a circular shape;
a suction tube extending through the sheath to the cauterizing tip with a suction opening in a central position of the circular shape of the cauterizing tip, the suction tube configured to draw fluid away from the cauterizing tip; and
at least one actuator configured to oscillate the cauterizing tip about an axis perpendicular to the longitudinal axis of the sheath concurrently with application of the current to cauterize the target area and mitigate tissue adherence of the target area to the cauterizing tip,
wherein the at least one actuator comprises at least one turbine in the sheath, the at least one turbine being unbalanced or eccentric;
wherein the at least one actuator comprises at least one piezoelectric transducer in the cauterizing tip, and wherein the piezoelectric transducer oscillates the cauterizing tip to mitigate tissue adherence of the target area to the tip;
wherein the at least one piezoelectric transducer comprises a plurality of piezoelectric transducers arranged in a circular array, and wherein, when electric current is sequentially applied to the plurality of piezoelectric transducers, a distal end of the cauterizing tip oscillates about the longitudinal axis.

16. The cautery device of claim 15, wherein the at least one turbine is actuated by fluid flowing through the suction tube and an irrigation tube.

* * * * *